United States Patent [19]
Ambrose

[11] Patent Number: 5,322,071
[45] Date of Patent: Jun. 21, 1994

[54] FLUID COLLECTION DEVICE

[75] Inventor: Julia T. Ambrose, Marietta, Ga.

[73] Assignee: Kimberly-Clark Corporation, Nenah, Wis.

[21] Appl. No.: 31,091

[22] Filed: Mar. 12, 1993

Related U.S. Application Data

[63] Continuation of Ser. No. 631,135, Dec. 20, 1990.

[51] Int. Cl.⁵ ............ A61B 19/00; A61B 19/09; A61M 1/00
[52] U.S. Cl. .................. 128/849; 128/853; 661/322; 661/356
[58] Field of Search .............. 128/849-856; 604/317, 355-357, 318, 332, 327, 322-326, 346-349, 328-331; 383/105, 107, 108, 113, 120, 907; 229/1.5, 4.5, 3.1; 206/522, 622; 220/62, 66, 67, 78, 79, DIG. 13; 4/450-457, 114.1, 144.1-144.4

[56] References Cited

U.S. PATENT DOCUMENTS

| | | | |
|---|---|---|---|
| 1,143,046 | 6/1915 | Gilmore | 604/352 |
| 1,597,556 | 8/1926 | Townsend | 604/357 |
| 2,337,648 | 12/1943 | Clarke | 4/451 |
| 2,491,799 | 12/1949 | Clarke | 604/355 |
| 3,613,676 | 10/1977 | Endres | 128/856 |
| 3,707,964 | 1/1973 | Patience et al. | 128/856 |
| 3,769,971 | 11/1973 | Collins | 128/856 |
| 4,007,741 | 2/1972 | Waldrop et al. | 604/357 |
| 4,076,017 | 2/1978 | Haswell | 604/357 |
| 4,105,019 | 8/1978 | Haswell | 604/357 |
| 4,149,537 | 4/1979 | Haswell | 128/292 |
| 4,681,573 | 7/1987 | McGovern | 604/329 |
| 4,751,751 | 6/1988 | Reno | 4/144.4 |
| 4,869,271 | 9/1989 | Idris | 604/356 |
| 4,890,628 | 1/1990 | Jackson | 128/849 |
| 4,974,604 | 12/1990 | Morris | 128/853 |
| 5,002,069 | 3/1991 | Thompson et al. | 604/356 |
| 5,052,554 | 10/1991 | Leonard | 583/906 |

FOREIGN PATENT DOCUMENTS

| | | | |
|---|---|---|---|
| 3032792 | 4/1982 | Fed. Rep. of Germany | 604/329 |
| 2133981 | 1/1984 | United Kingdom | 4/451 |

Primary Examiner—Randall L. Green
Assistant Examiner—K. M. Reichle
Attorney, Agent, or Firm—Patrick C. Wilson

[57] ABSTRACT

Disclosed herein is a fluid collection pouch which is extremely simple in design. The pouch utilizes a blank of fluid impervious material having a generally triangular shape including a first side and a second side joined at a common end point to themselves and at their distal ends to opposite ends of a third side. By joining the first and second sides to one another a fluid receiving chamber is formed with the third side forming an open end to the chamber and the joined distal ends of the first and second sides forming a flap portion which extends above the open end of the chamber. The fluid collection pouch is particularly well-suited for use in surgical procedures in which case it may be joined to a surgical drape in the expected path of fluid run-off or provided with a fenestration in the flap portion for registry with a corresponding fenestration in the surgical drape.

5 Claims, 3 Drawing Sheets

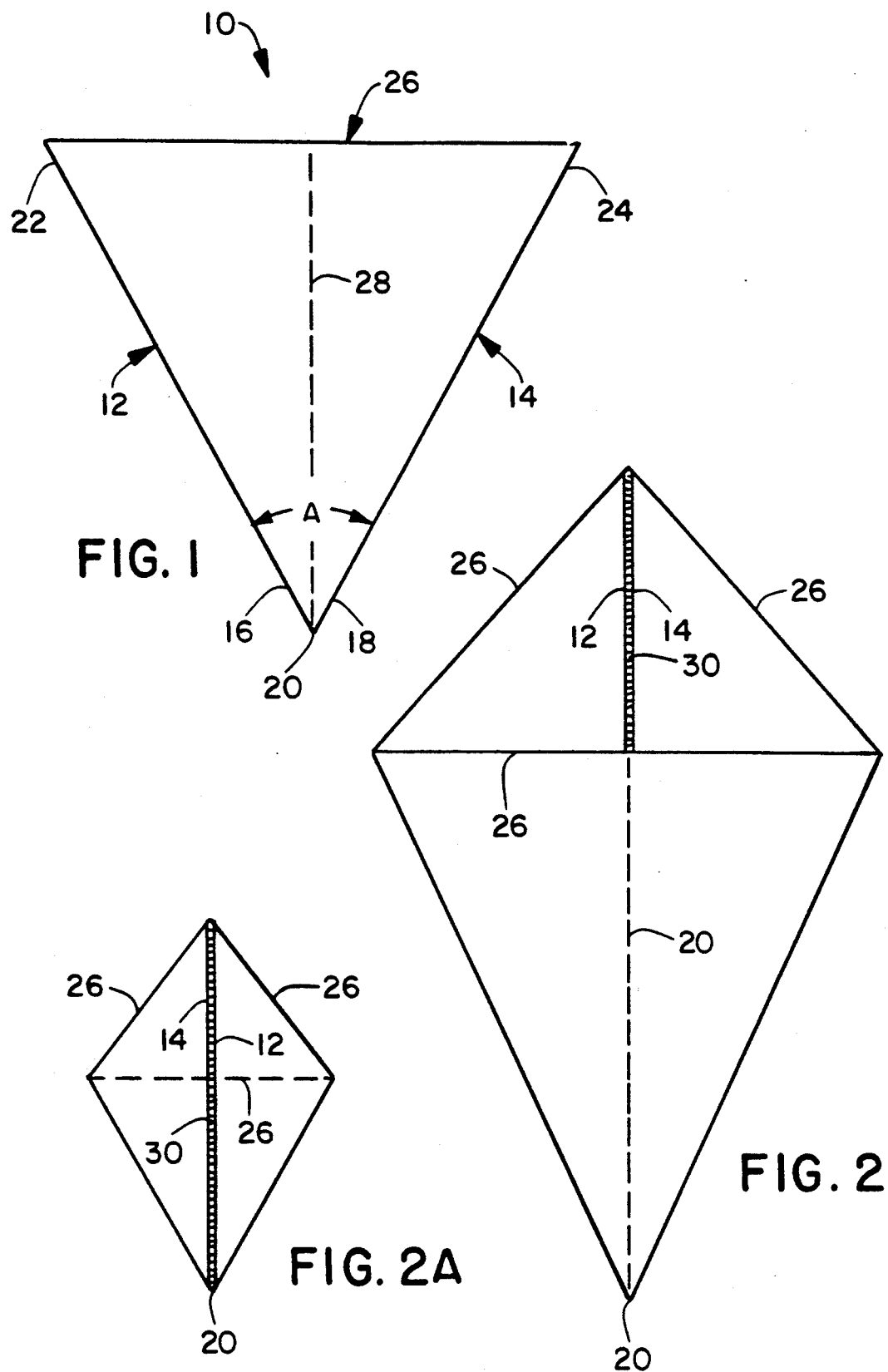

FLUID COLLECTION DEVICE

This is a continuation of copending application Ser. No. 07/631,135 filed on Dec. 20, 1991, now abandoned.

FIELD OF THE INVENTION

The present invention relates to a fluid collection pouch for collecting and retaining fluids. The pouch is particularly well suited for use in conjunction with surgical drapes for collecting body and irrigation fluids.

BACKGROUND OF THE INVENTION

A wide number of surgical procedures involve the use or generation of relatively large amounts of fluids such as blood and irrigation liquids. These fluids are often collected in pouches or bags which are either built into the surgical drape of later affixed to drape of patient in the expected path of fluid run-off. Oftentimes such pouches are not added to the surgical drape due to the expense of the pouch itself. It is therefore an object of the present invention to provide a fluid collection pouch that is extremely simple in design and manufacture thereby helping to reduce the cost of the product whether it is a stand alone item or incorporated directly into an overall drape design. This and other objects of the present invention will become more apparent upon a further review of the following specification, drawings and claims.

SUMMARY OF THE INVENTION

The present invention relates to a fluid collection pouch, extremely simple in design, which is adapted for use in surgical procedures for collecting body and irrigation fluids. The fluid collection pouch is made from either a fluid impervious material such as plastic film or fluid pervious material such as a nonwoven which has been made impervious by saturation or lamination. Generation of the pouch first involves cutting the fluid impervious material into a blank having at least three sides including a first side and a second side substantially equal in length. The first and second sides are joined to one another at one end with their distal ends being joined to opposite ends of a third side. Generally the third side will be straight thereby forming the hypotenuse of a triangle with the first and second sides. It is also possible, however, for the third side or edge to be curved or to be multi-sided.

To form the fluid collection pouch of the present invention, the blank of material is defined as having an axis extending from the commonly joined ends of the first and second sides and bisecting the third side or hypotenuse. The blank is folded such that the first and second sides are joined and seamed to form a fluid impervious seam which is in generally parallel juxtaposition with the axis. As a result, a fluid receiving pouch is defined with the hypotenuse forming the opening to the pouch. By this folding and seaming method the distal ends of the first and second sides extend beyond the opening to form a flap portion which can be used to secure the pouch directly to the patient or a surgical drape in the expected path of fluid run-off. If desired, the flap portion of the fluid collection pouch can include a fenestration which can be placed in vertical registry with a generally coextensive fenestration in the surgical drape.

BRIEF DESCRIPTION OF THE DRAWINGS

FIG. 1 depicts a blank of material suitable for use in forming the fluid collection pouch of the present invention.

FIG. 2 depicts the front of the blank from FIG. 1 with the first and second sides being folded over adjacent one another in substantially parallel juxtaposition with the axis of the blank material. These two sides are in turn seamed to form the fluid collection pouch of the present invention.

FIG. 2A depicts the back of the blank from FIG. 1 with the first and second sides being folded over adjacent one another in substantially parallel juxtaposition with the axis of the blank material. These two sides are in turn seamed to form the fluid collection pouch of the present invention.

DETAILED DESCRIPTION OF THE INVENTION

Figure 3:
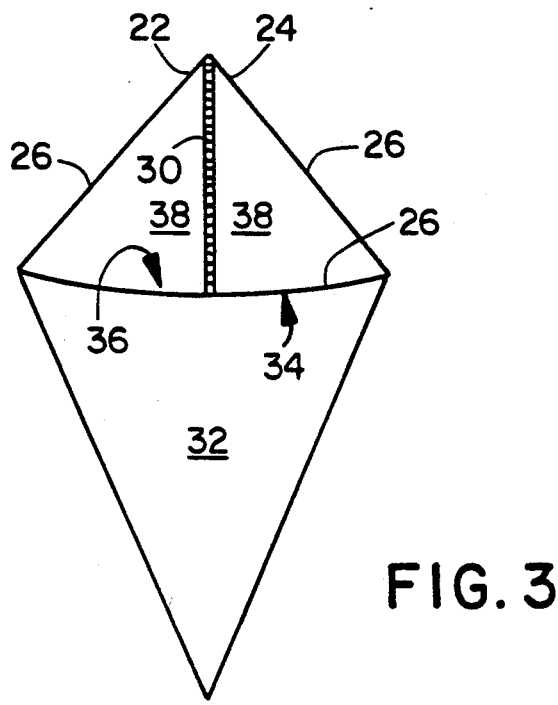
FIG. 3 is a front view of the fluid collection pouch of FIGS. 1, 2 and 2A once formed.

The fluid collection pouch of the present invention is shown and described in conjunction with its use with surgical room procedures and equipment including surgical drapes. It should be appreciated, however, that the fluid collection pouch of the present invention is readily usable in any application where fluid collection is required. As a result, the present description of the invention should not be considered as a limitation to scope of the present invention.

Referring of FIG. 1, there is shown a blank 10 of material used in the creation of the present invention. The blank 10 should be made from a fluid impervious material such as a polyethylene film or other polyolefin/plastic film material or a material which can be made fluid impervious. The material can be made form a woven or nonwoven material which has been made fluid impervious such as by lamination to a film or by saturation or coating with a barrier material such as latex. Another requirement for the material chosen is that it should be capable of being sterilized by one or all of steam, ethylene oxide gas and radiation sterilization techniques. In addition, the edges of the material should be capable of being seamed by the use of heat, adhesives and other means.

Referring again to FIG. 1, the blank 10 should have at least three sides in which case it can be described as being generally triangular in shape. The first side 12 and second side 14 should be substantially equal in length each having a first end 16 and 18 respectively which are joined together at a common point 20 thereby forming a first angle A. The opposite or distal ends 22 and 24 of the first and second sides 12 and 14 are separated by and connected to opposite ends of a third side or hypotenuse 26 thereby forming the generally triangular shape. To assist in defining the present invention, the blank 10 can be defined as having a longitudinal axis 28 extending from the common point 20 and bisecting the third side or hypotenuse 26 as well as first angle A. To form the pouch of the present invention, the blank 10 can be folded and seamed in at least two ways.

Referring to FIGS. 2 and 2A, the first and second sides 12 and 14 can each be folded inwardly such that they are in generally overlying parallel juxtaposition to the longitudinal axis 28. The two sides 12 and 14 can then be joined to one another along their length to form a seam 30. This seam can be formed by any number of means, including, but not limited to, ultrasonic or heat sealing, gluing and taping. Referring to FIG. 3, having formed the seam 30, a pouch 32 is formed having an open end 34 and a fluid receiving chamber 36. The open end 34 is formed by the hypotenuse 26 with the joined distal ends 22 and 24 of the first and second sides 12 and 14, respectively, forming a flap 38 which extends above the open end 34 of the pouch 32 and which is useful as a means for securing the pouch 32 to a surgical drape or other substrate including the human body (not shown). To ensure that the flap portion 38 is sufficiently large so as to aid fluid channeling into the open end 34 of the pouch 36, the hypotenuse 26 in a preferred construction is equal in length to the length of said first side 12 and, in a more preferred construction, the hypotenuse is at least one and one half times the length of the first side 12.

Figure 4:
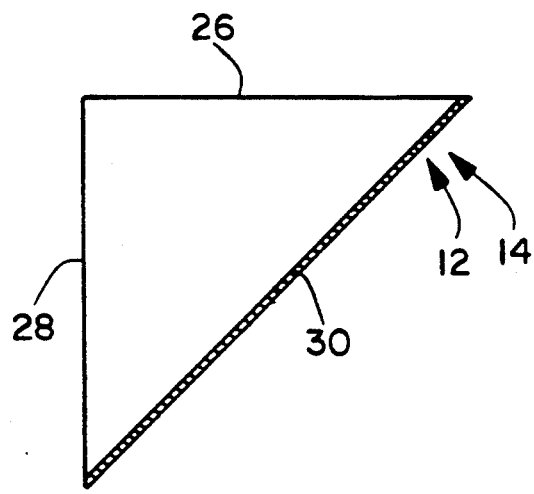
FIG. 4 is a view of a blank material suitable for use in forming the fluid collection pouch of the present invention being folded over on its axis such that the first and second sides are in overlapping relationship so that they can be seamed.
Figure 5:
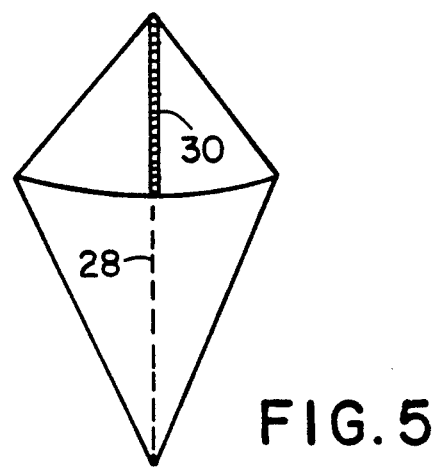
FIG. 5 is the fluid collection pouch of FIG. 4 being folded such that the seam is in overlapping relationship with the axis.

A second method of forming the fluid collection pouch 32 of the present invention is shown in FIGS. 4 and 5 with like reference numbers being used for like elements. In this configuration the first side 12 is folded over along axis 28 such that the first side 12 is in substantial alignment with the second side 14. The first and second sides 12 and 14 can then be joined to form a seam 30 in the same fashion as with the embodiment shown in FIGS. 1 through 3, thereby forming the fluid collection pouch 32. To shape the fluid collection pouch 32 into the same configuration as shown in FIG. 3, including a flap portion 38, the seam 30 can be folded toward the longitudinal axis 28 in a substantially overlapping fashion. See FIG. 5.

Figure 6:
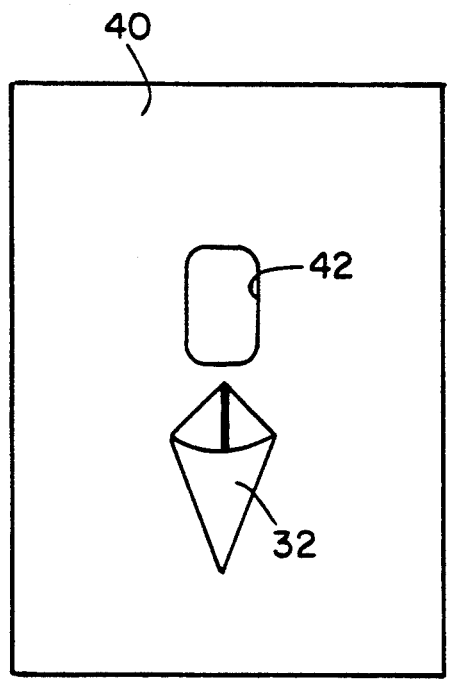
FIG. 6 depicts a fluid collection pouch joined to a surgical drape in accordance with the present invention.
Figure 7:
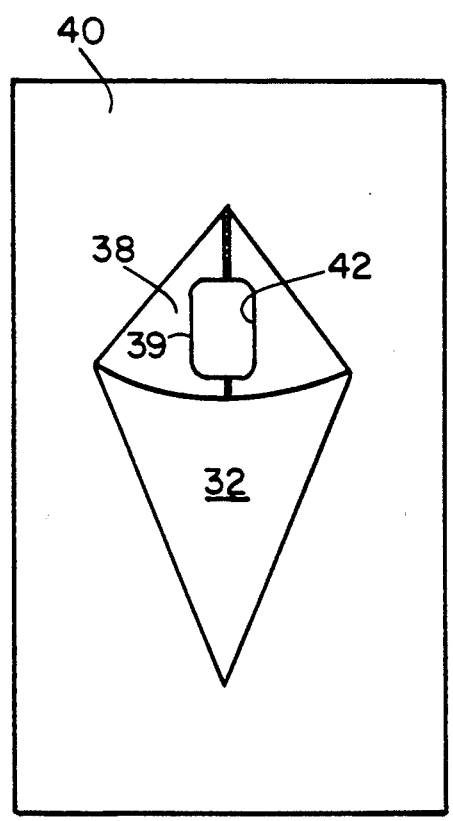
FIG. 7 depicts a fluid collection pouch joined to a surgical drape with both the drape and the pouch having fenestrations in vertical registry with one another according to the present invention.

If desired, the fluid collection pouch 32 of the present invention may be joined to a surgical drape 40 adjacent a fenestration 42 in the drape 40 and in the expected path of fluid run-off. See FIG. 6. Alternatively, the flap portion 38 may be provided with its own pouch fenestration 39 in registry with the fenestration 42 of the surgical drape. See FIG. 7.

Having thus described the invention in detail, it should be appreciated that various modifications and changes can be made in the present invention without departing form the spirit and scope of the following claims.

We claim:
1. A fluid collection system comprising:
a fluid impervious material having at least three sides including a first side and a second side, said first side and said second side being substantially equal in length and each having a first end and a distal end with said first ends forming a common endpoint, said first and second sides being folded over and joined to one another by a fluid impervious continuous seam from said common endpoint to said distal ends to form a fluid collection pouch having a fluid receiving chamber with an opening defined by said third side for receiving fluids, distal end portions of said first and second sides and opposite end portions of said third side forming a flap portion extending above a middle portion of said third side,
said fluid collection pouch being joined to a surgical drape with said opening of said fluid receiving chamber located in an expected path of fluid run-off, said flap portion defining a pouch fenestration and said surgical drape defining a fenestration, said pouch fenestration being in registry with said fenestration in said surgical drape.

2. A fluid collection system comprising:
a fluid impervious material having a generally triangular shape including a first side and a second side, said first and second sides each having a first end and a distal end, said first ends being joined to one another to form a common endpoint and the distal ends of the first and second sides being joined to opposite ends of a third side, said fluid impervious material further defining an axis extending from said common endpoint through and bisecting said third side, said first and second sides being folded over in generally parallel juxtaposition with said axis, said first and second sides being joined by a fluid impervious continuous seam from said common endpoint to said distal ends to form a fluid collection pouch having a fluid receiving chamber with an opening for receiving fluids defined by said third side, distal end portions of said first and second sides and opposite end portions of said third side extending above a middle portion of said third side,
said fluid collection pouch being joined to a surgical drape with said opening of said fluid receiving chamber located in an expected path of fluid run-off.

3. The fluid collection system of claim 2 wherein said flap portion defines a pouch fenestration and wherein said surgical drape defines a fenestration, said pouch fenestration being in registry with said fenestration in said surgical drape.

4. A fluid collection system comprising:
a fluid impervious material having a generally triangular shape including a first side and a second side, said first and second sides each having a first end and a distal end, said first ends being joined to form a common endpoint and the distal ends of said first and second sides being joined to opposite ends of a third side, said fluid impervious material defining an axis extending from said common endpoint through and bisecting said third side, said material being folded along said axis and said first and second sides being sealed to one another by a fluid impervious seal from said common endpoint to said distal ends to form a fluid collection pouch having a fluid receiving chamber with an opening for receiving fluids defined by said third side, said seam being juxtaposed with said axis so that distal end portions of said first and second sides and opposite end portions of said third extend above a middle portion of said third side to form a flap portion,
said fluid collection pouch being joined to a surgical drape with said opening of said fluid receiving chamber located in an expected path of fluid run-off.

5. The fluid collection system of claim 4 wherein said flap portion defines a pouch fenestration and wherein said surgical drape defines a fenestration, said pouch fenestration being in registry with said fenestration in said surgical drape.

* * * * *